US006080722A

United States Patent [19]
Soppet et al.

[11] Patent Number: 6,080,722
[45] Date of Patent: Jun. 27, 2000

[54] COLON SPECIFIC GENE AND PROTEIN

[75] Inventors: Daniel R. Soppet, Centreville, Va.; Yi Li; Patrick J. Dillon, both of Gaithersburg, Md.

[73] Assignee: Human Genome Sciences, Inc., Rockville, Md.

[21] Appl. No.: 09/162,508

[22] Filed: Sep. 29, 1998

Related U.S. Application Data

[62] Division of application No. 08/468,413, Jun. 6, 1995, Pat. No. 5,861,494.

[51] Int. Cl.⁷ .............................. A61K 38/00; C07K 1/00; C12P 21/06; C12N 1/20; C12N 15/00
[52] U.S. Cl. .................. 514/12; 435/69.1; 435/320.1; 435/252.3; 536/23.1; 536/23.5; 530/350
[58] Field of Search ................... 435/69.1; 536/23.1, 536/23.5; 530/350; 514/12

[56] References Cited

U.S. PATENT DOCUMENTS

| | | | |
|---|---|---|---|
| 4,683,202 | 7/1987 | Mullis | 435/91 |
| 5,380,645 | 1/1995 | Vogelstein | 435/6 |
| 5,837,841 | 11/1998 | Bandman et al. | 536/23.5 |

OTHER PUBLICATIONS

Singh et al., Carcinogenesis, 15(7):1317–1323 (1994).
Ueda et al., Gastroenterology, 104(4):911–917 (1993).
O'Connell, Cancer Supplement, 70(6):1732–1739 (1992).
Mount et al., Cancer Research, 54(23):6160–6166 (1994).
The New England Biolabs Catalog 1993–94 Edition, pp. 92–95.
Nicolaides et al., Nature, 371:75–80 (1994).
Geneseq Database, W37866, W37929, Aug. 21, 1998.

*Primary Examiner*—Rebecca E. Prouty
*Assistant Examiner*—M. Monshipouri
*Attorney, Agent, or Firm*—Human Genome Sciences, Inc.

[57] ABSTRACT

Human colon specific gene polypeptides and DNA (RNA) encoding such polypeptides and a procedure for producing such polypeptides by recombinant techniques is disclosed. Also disclosed are methods for utilizing such polynucleotides or polypeptides as a diagnostic marker for colon cancer and as an agent to determine if colon cancer has metastasized. Also disclosed are antibodies specific to the colon specific gene polypeptides which may be used to target cancer cells and be used as part of a colon cancer vaccine. Methods of screening for agonists and antagonists for the polypeptide and therapeutic uses of the antagonists are also disclosed.

19 Claims, 3 Drawing Sheets

FIG. 1A

```
                                    10         20         30         40         50
  1   GCACGAGGCCAAAACAGATTTGCAGATCAAGGAGAACCCAGGAGTTTCAAAGAAGCGCTAG         60

70         80         90        100        110
 61   TAAGGTCTCTGAGATCCTTGCACTAGTACATCCTCAGGGTAGGAGGAAGATGGCTTCCA         120
                                                       M  A  S            4

130        140        150        160        170
121   GAAGCATGGGCTGCTCCTATTGCTGAGCTGCCTGGCCAAAACAGGAGTCCTGGGTGATA         180
       S  M  R  L  L  L  L  S  C  L  A  K  T  G  V  L  G  D  I           24

190        200        210        220        230
181   TCATCATGAGACCCAGCTGTGCTCCTGGATGGTTTTACCACAGTCCAATTGCTATGGTT         240
       I  M  R  P  S  C  A  P  G  W  F  Y  H  K  S  N  C  Y  G  Y        44

250        260        270        280        290
241   ACTTCAGGAAGCTGAGGAACTGGTCTGATGCCGAGCTCGAGTGTCAGTCTTACGGAAACG         300
       F  R  K  L  R  N  W  S  D  A  E  L  E  C  Q  S  Y  G  N  G        64

310        320        330        340        350
301   GAGCCCACCTGGCATCTATCTGAGTTTAAAGGAAGCCAGCACCATAGCAGAGTACATAA         360
       A  H  L  A  S  I  L  S  L  K  E  A  S  T  I  A  E  Y  I  S        84

370        380        390        400        410
361   GTGGCTATCAGAGAAGCCAGCCGATATGGATTGGCCTGCACGACCCACAGAAGAGGCAGC         420
       G  Y  Q  R  S  Q  P  I  W  I  G  L  H  D  P  Q  K  R  Q  Q       104
```

FIG. 1B

```
                      430                  450                    470
421  AGTGGCAGTGGATTGATGGGGCCATGTATCTGTACAGATCCTGGTCTGGCAAGTCCATGG   480
105   S  G  S  G  I  D  G  A  M  Y  L  Y  R  S  W  S  G  K  S  M  G   124

490                  510                    530
481  GTGGGAACAAGCACTGTGCTGAGATGAGCTCCAATAACAACTTTTAACTTGGAGCAGCA   540
125   G  N  K  H  C  A  E  M  S  S  N  N  N  F  L  T  W  S  S  N   144

550                  570                    590
541  ACGAATGCAACAAGCGCCAACACTTCCTGTGCAAGTACCGACCATAGAGCAAGAATCAAG   600
145   E  C  N  K  R  Q  H  F  L  C  K  Y  R  P  *                164

610                  630                    650
601  ATTCTGCTAACTCCTGCACAGCCCCGTCCTCTTCCTTCTGCTAGCCTGGCTAAATCTGC    660

670                  690                    710
661  TCATTATTTCAGAGGGGAAACCTAGCAAACTAAGAGTGATAAGGGCCCTACTACACTGGC   720

730                  750                    770
721  TTTTTTAGGCTTAGAGACAGAAACTTTAGCATTGGCCCAGTAGTGGCTTCTAGCTCTAAA   780

790                  810                    830
781  TGTTTGCCCCGCCATCCCCTTTCCACAGTATCCTTCTTCCTCCCCCTGTCTCTGGCTG     840
```

FIG. 1C

```
                           850                        870                        890
841    TCTCGAGCAGTCTAGAAGAGTGCATCTCCAGCCTATGAAACAGCTGGGTCTTTGGCCATA    900
                           910                        930                        950
901    AGAAGTAAAGATTTGAAGACAGAAGGAAGAAACTCAGGAGTAAGCTTCTAGACCCCTTCA    960
                           970                        990                        1010
961    GCTTCTACACCCCTTCTGCCCCTCTCTCCATTGCCTGCACCCCAGCCACTCAACTCC      1020
                           1030                       1050                       1070
1021   TGCTTGTTTTCCTTTGGCCATAGGAAGGTTTACCAGTAGAATCCTTGCTAGGTTGATGT    1080
                           1090                       1110
1081   GGGCCATACATTCCTTTAATAAACCATTGTGTAC   1114
```

COLON SPECIFIC GENE AND PROTEIN

This application is a Divisional of U.S. application Ser. No. 08/468,413 filed Jun. 6, 1995 now U.S. Pat. No. 5,861,494, issued on Jan. 19, 1999.

This invention relates to newly identified polynucleotides, polypeptides encoded by such polynucleotides, and the use of such polynucleotides and polypeptides. The present invention further relates to inhibiting the production and function of the polypeptides of the present invention.

The gastrointestinal tract is the most common site of both newly diagnosed cancers and fatal cancers occurring each year in the USA, figures are somewhat higher for men than for women. The incidence of colon cancer in the USA is increasing, while that of gastric cancer is decreasing, cancer of the small intestine is rare. The incidence of gastrointestinal cancers varies geographically. Gastric cancer is common in Japan and uncommon in the United States, whereas colon cancer is uncommon in Japan and common in the USA. An environmental etiologic factor is strongly suggested by the statistical data showing that people who move to a high-risk area assume the high risk. Some of the suggested etiologic factors for gastric cancer include aflatoxin, a carcinogen formed by *aspergillus flavus* and present in contaminated food, smoked fish, alcohol, and Vitamin A and magnesium deficiencies. A diet high in fat and low in bulk, and, possibly, degradation products of sterol metabolism may be the etiologic factors for colon cancer. Certain disorders may predispose to cancer, for example, pernicious anemia to gastric cancer, untreated non-tropical sprue and immune defects to lymphoma and carcinoma, and ulcerative and granulomatous colitis, isolated polyps, and inherited familial polyposis to carcinoma of the colon.

The most common tumor of the colon is adenomatous polyp. Primary lymphoma is rare in the colon and most common in the small intestine.

Adenomatous polyps are the most common benign gastrointestinal tumors. They occur throughout the GI tract, most commonly in the colon and stomach, and are found more frequently in males than in females. They may be single, or more commonly, multiple, and sessile or pedunculated. They may be inherited, as in familial polyposis and Gardener's syndrome, which primarily involves the colon. Development of colon cancer is common in familial polyposis. Polyps often cause bleeding, which may occult or gross, but rarely cause pain unless complications ensue. Papillary adenoma, a less common form found only in the colon, may also cause electrolyte loss and mucoid discharge.

A malignant tumor includes a carcinoma of the colon which may be infiltrating or exophytic and occurs most commonly in the rectosigmoid. Because the content of the ascending colon is liquid, a carcinoma in this area usually does not cause obstruction, but the patient tends to present late in the course of the disease with anemia, abdominal pain, or an abdominal mass or a palpable mass.

The prognosis with colonic tumors depends on the degree of bowel wall invasion and on the presence of regional lymph node involvement and distant metastases. The prognosis with carcinoma of the rectum and descending colon is quite unexpectedly good. Cure rates of 80 to 90% are possible with early resection before nodal invasion develops. For this reason, great care must be taken to exclude this disease when unexplained anemia, occult gastrointestinal bleeding, or change in bowel habits develop in a previously healthy patient. Complete removal of the lesion before it spreads to the lymph nodes provides the best chance of survival for a patient with cancer of the colon. Detection in an asymptomatic patient by occult-bleeding, blood screening results in the highest five year survival.

Clinically suspected malignant lesions can usually be detected radiologically. Polyps less than 1 cm can easily be missed, especially in the upper sigmoid and in the presence of diverticulosis. Clinically suspected and radiologically detected lesions in the esophagus, stomach or colon can be confirmed by fiber optic endoscopy combined with histologic tissue diagnosis made by directed biopsy and brush sitology. Colonoscopy is another method utilized to detect colon diseases. Benign and malignant polyps not visualized by X-ray are often detected on colonoscopy. In addition, patients with one lesion on X-ray often have additional lesions detected on colonoscopy. Sigmoidoscope examination, however, only detects about 50% of colonic tumors.

The above methods of detecting colon cancer have drawbacks, for example, small colonic tumors may be missed by all of the above-described methods. The importance of detecting colon cancer is also extremely important to prevent metastases.

In accordance with an aspect of the present invention, there are provided nucleic acid probes comprising nucleic acid molecules of sufficient length to specifically hybridize to the RNA transcribed from the human colon specific gene of the present invention or to DNA corresponding to such RNA.

In accordance with another aspect of the present invention there is provided a method of and products for diagnosing colon cancer metastases by determining the presence of RNA transcribed from the human colon specific gene of the present invention or DNA corresponding to such RNA in a sample derived from a host.

In accordance with yet another aspect of the present invention, there is provided a method of and products for diagnosing colon cancer metastases by detecting an altered level of a polypeptide corresponding to the colon specific gene of the present invention in a sample derived from a host, whereby an elevated level of the polypeptide indicates a colon cancer diagnosis.

In accordance with another aspect of the present invention, there are provided isolated polynucleotides encoding a polypeptide of the present invention, including mRNAs, DNAs, cDNAs, genomic DNAs, as well as antisense analogs and biologically active and diagnostically or therapeutically useful fragments thereof.

In accordance with a further aspect of the present invention, there are provided novel polypeptide encoded by the polynucleotides, as well as biologically active and diagnostically or therapeutically useful fragments, analogs and derivatives thereof.

In accordance with yet a further aspect of the present invention, there is provided a process for producing such polypeptides by recombinant techniques comprising culturing recombinant prokaryotic and/or eukaryotic host cells, containing a polynucleotide of the present invention, under conditions promoting expression of said proteins and subsequent recovery of said proteins.

In accordance with yet a further aspect of the present invention, there are provided antibodies specific to such polypeptides.

In accordance with another aspect of the present invention, there are provided processes for using the polypeptides of the present invention to treat colon cancer and for using the polypeptide to screen for compounds which interact with the polypeptides, for example, compounds which inhibit or activate the receptor for the polypeptide of the present invention.

In accordance with yet another aspect of the present invention, there is provided a process to screen for compounds which interact with the polypeptides, for example, compounds which inhibit or activate the polypeptides of the present invention.

In accordance with yet a further aspect of the present invention, there are provided processes for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1C show the cDNA sequence and the corresponding deduced amino acid sequence for the human colon specific gene disclosed in this application. The standard one-letter abbreviations for amino acids are used.

The term "colon specific gene" means that such gene is primarily expressed in tissues derived from the colon, and such gene may be expressed in cells derived from tissues other than from the colon. However, the expression of such gene is significantly higher in tissues derived from the colon than from non-colon tissues.

In accordance with an aspect of the present invention, there are provided isolated nucleic acids (polynucleotides) which encode for the mature polypeptide having the deduced amino acid sequence of FIGS. 1A–1C collectively (SEQ ID NO:2) or for the mature polypeptide encoded by the cDNA of the clone(s) deposited as ATCC Deposit No. 97129 on Apr. 28, 1995.

The ATCC number referred to above is directed to a biological deposit with the ATCC, 10801 University Boulevard, Manassas, Va. 20110-2209. The strain referred to is being maintained under the terms of the Budapest Treaty and will be made available to a patent office signatory to the Budapest Treaty.

A polynucleotide encoding the colon specific gene of the present invention was isolated from a human colon cancer cDNA library. The polynucleotide contains an open reading frame encoding a protein of 158 amino acid residues. The polypeptide exhibits structural homology to a galactose specific lectin from a diamondback rattlesnake with 36% identity and 54% similarity over a 125 amino acid stretch and 30% identity and 52% similarity to a human pancreatic stone protein precursor.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequence shown in FIGS. 1A–1C collectively (SEQ ID NO:1) or that of the deposited clone(s) or may be a different coding sequence which coding sequence, as a result of the redundancy or degeneracy of the genetic code, encodes the same mature polypeptides as the DNA of FIGS. 1A–1C collectively (SEQ ID NO:1) or the deposited cDNA.

The polynucleotides which encode for the mature polypeptide of FIGS. 1A–1C collectively (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1C collectively (SEQ ID NO:2) or the polypeptide encoded by the cDNA of the deposited clone(s). The variants of the polynucleotides may be a naturally occurring allelic variant of the polynucleotides or a non-naturally occurring variant of the polynucleotides.

Thus, the present invention includes polynucleotides encoding the same mature polypeptide as shown in FIGS. 1A–1C collectively (SEQ ID NO:2) or the same mature polypeptide encoded by the cDNA of the deposited clone(s) as well as variants of such polynucleotides which variants encode for a fragment, derivative or analog of the polypeptide of FIGS. 1A–1C collectively (SEQ ID NO:2) or the polypeptide encoded by the cDNA of the deposited clone(s). Such nucleotide variants include deletion variants, substitution variants and addition or insertion variants.

As hereinabove indicated, the polynucleotides may have a coding sequence which is a naturally occurring allelic variant of the coding sequence shown in FIGS. 1A–1C collectively (SEQ ID NO:1) or of the coding sequence of the deposited clone(s). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotides of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length colon specific gene may be used as a hybridization probe for a cDNA library to isolate the full length gene and to isolate other genes which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete colon specific gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1C collectively (SEQ ID NO:1) or the deposited cDNA (s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of FIG. 1 (SEQ ID NO:1), for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of FIGS. 1A–1C collectively (SEQ ID NO:2) as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

In accordance with another aspect of the present invention there are provided polynucleotides which are preferably at least 10 base pairs in length and which hybridize to and are at least 70% identical to RNA (or corresponding DNA) transcribed from a human gene which has a coding sequence which is at least 90% identical to coding sequence of the DNA sequence of FIGS. 1A–1C collectively (SEQ ID NO:1).

Thus, the polynucleotide sequences which hybridize as described above may be used to hybridize to and detect the expression of the human gene to which they correspond for use in diagnostic assays as hereinafter described.

In accordance with still another aspect of the present invention there are provided diagnostic assays for detecting micrometastases of colon cancer in a host. While applicant does not wish to limit the reasoning of the present invention to any specific scientific theory, it is believed that the presence of active transcription of a colon specific gene of the present invention in cells of the host, other than those derived from the colon, is indicative of colon cancer metastases. This is true because, while the colon specific gene are found in all cells of the body, their transcription to mRNA, cDNA and expression products is primarily limited to the colon in non-diseased individuals. However, if colon cancer is present, colon cancer cells migrate from the cancer to other cells, such that these other cells are now actively transcribing and expressing a colon specific gene at a greater level than is normally found in non-diseased individuals, i.e., transcription is higher than found in non-colon tissues in healthy individuals. It is the detection of this enhanced transcription or enhanced protein expression in cells, other than those derived from the colon, which is indicative of metastases of colon cancer.

In one example of such a diagnostic assay, an RNA sequence in a sample derived from a tissue other than the colon is detected by hybridization to a probe. The sample contains a nucleic acid or a mixture of nucleic acids, at least one of which is suspected of containing RNA (or corresponding cDNA) transcribed from a human colon specific gene of the present invention. Thus, for example, in a form of an assay for determining the presence of a specific RNA in cells, initially RNA is isolated from the cells.

A sample may be obtained from cells derived from tissue other than from the colon including but not limited to blood, urine, saliva, tissue biopsy and autopsy material. The use of such methods for detecting enhanced transcription to mRNA from a human colon specific gene of the present invention or fragment thereof in a sample obtained from cells derived from other than the colon is well within the scope of those skilled in the art from the teachings herein.

The isolation of mRNA comprises isolating total cellular RNA by disrupting a cell and performing differential centrifugation. Once the total RNA is isolated, mRNA is isolated by making use of the adenine nucleotide residues known to those skilled in the art as a poly(A) tail found on virtually every eukaryotic mRNA molecule at the 3' end thereof. Oligonucleotides composed of only deoxythymidine [oligo(dT)] are linked to cellulose and the oligo(dT)- cellulose packed into small columns. When a preparation of total cellular RNA is passed through such a column, the mRNA molecules bind to the oligo(dT) by the poly(A)tails while the rest of the RNA flows through the column. The bound mRNAs are then eluted from the column and collected.

One example of detecting isolated mRNA transcribed from a colon specific gene of the present invention or a fragment thereof which encodes for a polypeptide of the present invention, comprises screening the collected mRNAs with specific oligonucleotide probes which have been custom designed to hybridize to the mRNA to be detected. The oligonucleotide probe comprises a polynucleotide sequence which hybridizes to at least a portion of the mRNA (or cDNA produced from such RNA) transcribed from one or more of the colon specific gene of the present invention or fragment thereof. The polynucleotide sequences are at least 70% identical to and hybridize to mRNA (or cDNA produced from such RNA) transcribed from a human colon specific gene of the present invention having exons which includes DNA having at least 90%, preferably at least 95% identity and most preferably at least 97% identity to the DNA sequence of FIGS. 1A–1C collectively (SEQ ID NO:1).

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product.

An example of detecting a polynucleotide complementary to the mRNA sequence (cDNA) utilizes the polymerase chain reaction (PCR) in conjunction with reverse transcriptase. PCR is a very powerful method for the specific amplification of DNA or RNA stretches (Saiki et al., Nature, 234:163–166 (1986)). One application of this technology is in nucleic acid probe technology to bring up nucleic acid sequences present in low copy numbers to a detectable level. Numerous diagnostic and scientific applications of this method have been described by H. A. Erlich (ed.) in PCR Technology-Principles and Applications for DNA Amplification, Stockton Press, USA, 1989, and by M. A. Inis (ed.) in PCR Protocols, Academic Press, San Diego, USA, 1990.

RT-PCR is a combination of PCR with the reverse transcriptase enzyme. Reverse transcriptase is an enzyme which produces cDNA molecules from corresponding mRNA molecules. This is important since PCR amplifies nucleic acid molecules, particularly DNA, and this DNA may be produced from the mRNA isolated from a sample derived from the host.

A specific example of an RT-PCR diagnostic assay involves removing a sample from a tissue of a host. Such a sample will be from a tissue, other than the colon, for example, blood. Therefore, an example of such a diagnostic assay comprises whole blood gradient isolation of nucleated cells, total RNA extraction, RT-PCR of total RNA and agarose gel electrophoresis of PCR products. The PCR products comprise cDNA complementary to RNA transcribed from the colon specific gene of the present invention or fragments thereof. More particularly, a blood sample is obtained and the whole blood is combined with an equal volume of phosphate buffered saline, centrifuged and the lymphocyte and granulocyte layer is carefully aspirated and rediluted in phosphate buffered saline and centrifuged again. The supernate is discarded and the pellet containing nucleated cells is used for RNA extraction using the RNazole B method as described by the manufacturer (Tel-Test Inc., Friendswood, Tex.).

Oligonucleotide primers and probes are prepared with high specificity to the DNA sequences of the present invention. The probes are at least 10 base pairs in length, preferably at least 30 base pairs in length and may be at least 50 base pairs in length or more. The reverse transcriptase reaction and PCR amplification are performed sequentially without interruption. Taq polymerase is used during PCR and the PCR products are concentrated and the entire sample is run on a Tris-borate-EDTA agarose gel containing ethidium bromide.

In accordance with another aspect of the present invention, there is provided a method of diagnosing a disorder of the colon, for example colon cancer, by determining altered levels of the colon specific polypeptides of the present invention in a biological sample, derived from tissue other than from the colon. Elevated levels of the colon specific polypeptides of the present invention, indicates active transcription and expression of the corresponding colon specific gene product. Assays used to detect levels of a colon specific gene polypeptide in a sample derived from a host are well-known to those skilled in the art and include radioimmunoassays, competitive-binding assays, Western blot analysis, ELISA assays and "sandwich" assays. A biological sample may include, but is not limited to, tissue extracts, cell samples or biological fluids, however, in accordance with the present invention, a biological sample specifically does not include tissue or cells of the colon.

An ELISA assay (Coligan, et al., *Current Protocols in Immunology*, 1(2), Chapter 6, 1991) initially comprises preparing an antibody specific to a colon specific polypeptide of the present invention, preferably a monoclonal antibody. In addition, a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g., a polystyrene dish, that binds the proteins in the sample. Any free protein binding sites on the dish are then covered by incubating with a non-specific protein, such as BSA. Next, the monoclonal antibody is incubated in the dish during which time the monoclonal antibodies attach to the colon specific polypeptide attached to the polystyrene dish. All unbound monoclonal antibody is washed out with buffer. The reporter antibody linked to horseradish peroxidase is now placed in the dish resulting in binding of the reporter antibody to any monoclonal antibody bound to the colon specific gene polypeptide. Unattached reporter antibody is then washed out. Peroxidase substrates are then added to the dish and the amount of color developed in a given time period is a measurement of the amount of the colon specific polypeptide present in a given volume of patient sample when compared against a standard curve.

A competition assay may be employed where antibodies specific to a colon specific polypeptide are attached to a solid support. The colon specific polypeptide is then labeled and the labeled polypeptide a sample derived from the host are passed over the solid support and the amount of label detected, for example, by liquid scintillation chromatography, can be correlated to a quantity of the colon specific polypeptide in the sample.

A "sandwich" assay is similar to an ELISA assay. In a "sandwich" assay, colon specific polypeptides are passed over a solid support and bind to antibody attached to the solid support. A second antibody is then bound to the colon specific polypeptide. A third antibody which is labeled and is specific to the second antibody, is then passed over the solid support and binds to the second antibody and an amount can then be quantified.

In alternative methods, labeled antibodies to a colon specific polypeptide are used. In a one-step assay, the target molecule, if it is present, is immobilized and incubated with a labeled antibody. The labeled antibody binds to the immobilized target molecule. After washing to remove the unbound molecules, the sample is assayed for the presence of the label. In a two-step assay, immobilized target molecule is incubated with an unlabeled antibody. The target molecule-labeled antibody complex, if present, is then bound to a second, labeled antibody that is specific for the unlabeled antibody. The sample is washed and assayed for the presence of the label.

The choice of marker used to label the antibodies will vary depending upon the application. However, the choice of marker is readily determinable to one skilled in the art. These labeled antibodies may be used in immunoassays as well as in histological applications to detect the presence of the proteins. The labeled antibodies may be polyclonal or monoclonal.

The presence of active transcription, which is greater than that normally found, of the colon specific gene in cells other than from the colon, by the presence of an altered level of mRNA, cDNA or expression products is an important indication of the presence of a colon cancer which has metastasized, since colon cancer cells are migrating from the colon into the general circulation. Accordingly, this phenomenon may have important clinical implications since the method of treating a localized, as opposed to a metastasized, tumor is entirely different.

The assays described above may also be used to test whether bone marrow preserved before chemotherapy is contaminated with micrometastases of a colon cancer cell. In the assay, blood cells from the bone marrow are isolated and treated as described above, this method allows one to determine whether preserved bone marrow is still suitable for transplantation after chemotherapy.

Antibodies specific to the colon specific polypeptide, for example monoclonal antibodies, may also be used to target colon cancer cells, for example, in a method of homing interaction agents which, when contacting colon cancer cells, destroy them. This is true since the antibodies are specific for colon specific polypeptides which are primarily expressed in the colon, and a linking of the interaction agent to the antibody would cause the interaction agent to be carried directly to the prostate.

Antibodies of this type may also be used to do in vivo imaging, for example, by labeling the antibodies to facilitate scanning of the pelvic area and the colon. One method for imaging comprises contacting any tumor cells of the colon to be imaged with an anti-colon specific antibody labeled with a detectable marker. The method is performed under conditions such that the labeled antibody binds to any colon specific polypeptides. In a specific example, the antibodies interact with the colon, for example, colon cancer cells, and fluoresce upon such contact such that imaging and visibility of the colon is enhanced to allow a determination of the diseased or non-diseased state of the colon.

The present invention further relates to a colon specific gene polypeptide which has the deduced amino acid sequence of FIG. 1 (SEQ ID NO:2) or which have the amino acid sequences encoded by the deposited cDNA(s), as well as fragments, analogs and derivatives of such polypeptide.

The terms "fragment," "derivative" and "analog" when referring to the polypeptide of FIG. 1 (SEQ ID NO:2) or that encoded by the deposited cDNA(s), means a polypeptide which retains essentially the same biological function or activity as such polypeptide. Thus, an analog includes a proprotein which can be activated by cleavage of the proprotein portion to produce an active mature polypeptide.

The polypeptides of the present invention may be recombinant polypeptides, natural polypeptides or synthetic polypeptides, preferably recombinant polypeptides.

The fragment, derivative or analog of the polypeptides of FIGS. 1A–1C collectively (SEQ ID NO:2) or that encoded by the deposited cDNA(s) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of FIGS. 1A–1C collectively (SEQ ID NO:2) (in particular the mature polypeptide) as well as polypeptides which have at least 70% similarity (preferably at least 70% identity) to the polypeptide of FIGS. 1A–1C collectively (SEQ ID NO:2) and more preferably at least 90% similarity (more preferably at least 90% identity) to the polypeptide of FIGS. 1A–1C collectively (SEQ ID NO:2) and still more preferably at least 95% similarity (still more preferably at least 90% identity) to the polypeptide of FIGS. 1A–1C collectively (SEQ ID NO:2) and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the colon specific genes. The culture conditions, such as temperature, pH and the like, are those previously used with the host cell selected for expression, and will be apparent to those of ordinarily skill in the art.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E. coli$. lac or trp, the phage lambda $P_L$ promoter and other promoters known to control expression of gene in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker gene to provide a phenotypic trait for selection of transformed host cells such as dihydrofolate reductase or neomycin resistance for eukaryotic cell culture, or such as tetracycline or ampicillin resistance in $E. coli$.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E. coli$, Streptomyces, $Salmonella\ typhimurium$; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E. coli$ and $S. cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The colon specific gene polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polynucleotides of the present invention may have the coding sequence fused in frame to a marker sequence which allows for purification of the polypeptide of the present invention. An example of a marker sequence is a hexa-histidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptide of the present invention may be glycosylated or may be non-glycosylated. Polypeptides of the invention may also include an initial methionine amino acid residue.

In accordance with another aspect of the present invention there are provided assays which may be used to screen for therapeutics to inhibit the action of the colon specific gene or colon specific protein of the present invention. One assay takes advantage of the reductase function of these proteins. The present invention discloses methods for selecting a therapeutic which forms a complex with colon specific gene proteins with sufficient affinity to prevent their biological action. The methods include various assays, including competitive assays where the proteins are immobilized to a support, and are contacted with a natural substrate and a labeled therapeutic either simultaneously or in either consecutive order, and determining whether the therapeutic effectively competes with the natural substrate in a manner sufficient to prevent binding of the protein to its substrate.

In another embodiment, the substrate is immobilized to a support, and is contacted with both a labeled colon specific polypeptide and a therapeutic (or unlabeled proteins and a labeled therapeutic), and it is determined whether the amount of the colon specific polypeptide bound to the substrate is reduced in comparison to the assay without the therapeutic added. The colon specific polypeptide may be labeled with antibodies.

In another example of such a screening assay, there is provided a mammalian cell or membrane preparation expressing a colon specific polypeptide of the present invention incubated with elements which undergo simultaneous oxidation and reduction, for example hydrogen and oxygen which together form water, wherein the hydrogen could be labeled by radioactivity, e.g., tritium, in the presence of the compound to be screened under conditions favoring the oxidation reduction reaction where hydrogen and oxygen form water. The ability of the compound to block this interaction could then be measured.

This invention provides a method for identification of the receptors for the polypeptide of the present invention. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone (s) that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Further, since the colon specific gene and gene product of the present invention is a growth regulator agonist and antagonists to the polypeptide could be determined by an assay comprising combining membrane preparations comprising the receptor for the polypeptide and a compound to be screened and determining the generation of a signal from the receptor. In the case of determining an antagonist, the polypeptide of the present invention is added to the assay and the ability of the compound to compete for receptor sites, i.e., lack of generation of signal from receptor, could then be determined.

Potential antagonists to a colon specific polypeptide include antibodies and anti-idiotypic antibodies as described above, or in some cases, an oligonucleotide, which binds to the polypeptide.

Another potential antagonist is an antisense construct prepared using antisense technology, which is directed to a colon specific polynucleotide to prevent transcription. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of a colon specific polynucleotide. The antisense RNA oligonucleotide hybridizes to the mRNA in vivo and blocks translation of the mRNA molecule into the colon specific gene polypeptide (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the colon specific polypeptides.

Potential antagonists also include a small molecule which binds to and occupies the active site of the colon specific polypeptide thereby making the active site inaccessible to substrate such that normal biological activity is prevented. Examples of small molecules include but are not limited to small peptides or peptide-like molecules.

The antagonists may be employed to treat colon cancer, since they interact with the function of colon specific polypeptides in a manner sufficient to inhibit natural function which is necessary for the viability of colon cancer cells. The antagonists may be employed in a composition with a pharmaceutically acceptable carrier, e.g., as hereinafter described.

The polypeptides and antagonists of the present invention may be employed in combination with a suitable pharmaceutical carrier. Such compositions comprise a therapeutically effective amount of the polypeptide or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal, intra-anal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The colon specific gene polypeptides and antagonists and agonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding a polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CNV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E–86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of a colon specific gene of the present invention as a diagnostic. For example, some diseases result from inherited defective genes. The colon specific gene of the present invention is overexpressed in colon cancer. A mutation in a colon specific gene of the present invention at the DNA level may be detected by a variety of techniques. Nucleic acids used for diagnosis (genomic DNA, mRNA, etc.) may be obtained from a patient's cells, other than from the colon, such as from blood, urine, saliva, tissue biopsy and autopsy material. The genomic DNA may be used directly for detection or may be amplified enzymatically by using PCR (Saiki, et al., *Nature*, 324:163–166 (1986)) prior to analysis. RNA or cDNA may also be used for the same purpose. As an example, PCR primers complementary to the nucleic acid of the instant invention can be used to identify and analyze mutations in a colon specific polynucleotide of the present invention. For example, deletions and insertions can be detected by a change in size of the amplified product in comparison to the normal genotype. Point mutations can be identified by hybridizing amplified DNA to radiolabelled colon specific RNA or, alternatively, radiolabelled antisense DNA sequences.

Another well-established method for screening for mutations in particular segments of DNA after PCR amplification is single-strand conformation polymorphism (SSCP) analysis. PCR products are prepared for SSCP by ten cycles of reamplification to incorporate $^{32}$P-dCTP, digested with an appropriate restriction enzyme to generate 200–300 bp fragments, and denatured by heating to 85° C. for 5 min. and then plunged into ice. Electrophoresis is then carried out in a nondenaturing gel (5% glycerol, 5% acrylamide) (Glavac, D. and Dean, M., Human Mutation, 2:404–414 (1993)).

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotides or by automatic sequencing procedures with fluorescent-tags.

Genetic testing based on DNA sequence differences may be achieved by detection of alteration in electrophoretic mobility of DNA fragments and gels with or without denaturing agents. Small sequence deletions and insertions can be visualized by high-resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers, et al., *Science*, 230:1242 (1985)). In addition, sequence alterations, in particular small deletions, may be detected as changes in the migration pattern of DNA.

Sequence changes at specific locations may also be revealed by nuclease protection assays, such as Rnase and S1 protection or the chemical cleavage method (e.g., Cotton, et al., *PNAS, USA,* 85:4397–4401 (1985)).

Thus, the detection of the specific DNA sequence may be achieved by methods such as hybridization, RNase protection, chemical cleavage, direct DNA sequencing, or the use of restriction enzymes (e.g., Restriction Fragment Length Polymorphisms (RFLP)) and Southern blotting.

The sequences of the present invention are also valuable for chromosome identification. The sequence is specifically targeted to and can hybridize with a particular location on an individual human chromosome. Moreover, there is a current need for identifying particular sites on the chromosome.

Few chromosome marking reagents based on actual sequence data (repeat polymorphisms) are presently available for marking chromosomal location. The mapping of DNAs to chromosomes according to the present invention is an important first step in correlating those sequences with gene associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between gene and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Transgenic mice may also be used to generate antibodies.

The antibodies may also be employed to target colon cancer cells, for example, in a method of homing interaction agents which, when contacting colon cancer cells, destroy them. This is true since the antibodies are specific for the colon specific polypeptides of the present invention. A linking of the interaction agent to the antibody would cause the interaction agent to be carried directly to the colon.

Antibodies of this type may also be used to do in vivo imaging, for example, by labeling the antibodies to facilitate scanning of the pelvic area and the colon. One method for imaging comprises contacting any cancer cells of the colon to be imaged with an anti-colon specific protein-antibody labeled with a detectable marker. The method is performed under conditions such that the labeled antibody binds to the colon specific polypeptides. In a specific example, the antibodies interact with the colon, for example, colon cancer cells, and fluoresce upon contact such that imaging and visibility of the colon are enhanced to allow a determination of the diseased or non-diseased state of the colon.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Determination of Transcription of the Colon Specific Gene

To assess the presence or absence of active transcription of a colon specific gene RNA, approximately 6 ml of venous blood is obtained with a standard venipuncture technique using heparinized tubes. Whole blood is mixed with an equal volume of phosphate buffered saline, which is then layered over 8 ml of Ficoll (Pharmacia, Uppsala, Sweden) in a 15-ml polystyrene tube. The gradient is centrifuged at 1800×g for 20 min at 5° C. The lymphocyte and granulocyte layer (approximately 5 ml) is carefully aspirated and rediluted up to 50 ml with phosphate-buffered saline in a 50-ml tube, which is centrifuged again at 1800×g for 20 min. at 5° C. The supernatant is discarded and the pellet containing nucleated cells is used for RNA extraction using the RNazole B method as described by the manufacturer (Tel-Test Inc., Friendswood, Tex.).

To determine the quantity of mRNA from the gene of interest, a probe is designed with an identity to the mRNA sequence transcribed from a human gene whose coding portion includes a DNA sequence of FIG. 1. This probe is mixed with the extracted RNA and the mixed DNA and RNA are precipitated with ethanol −70° C. for 15 minutes). The pellet is resuspended in hybridization buffer and dissolved. The tubes containing the mixture are incubated in a 72° C. water bath for 10–15 mins. to denature the DNA. The tubes are rapidly transferred to a water bath at the desired hybridization temperature. Hybridization temperature depends on the G+C content of the DNA. Hybridization is done for 3 hrs. 0.3 ml of nuclease-S1 buffer is added and mixed well. 50 µl of 4.0 M ammonium acetate and 0.1 M EDTA is added to stop the reaction. The mixture is extracted with phenol/chloroform and 20 µg of carrier tRNA is added and precipitation is done with an equal volume of isopropanol. The precipitate is dissolved in 40 µl of TE (pH 7.4) and run on an alkaline agarose gel. Following electrophoresis, the RNA is microsequenced to confirm the nucleotide sequence. (See Favaloro, J. et al., Methods Enzymol., 65:718 (1980) for a more detailed review).

Two oligonucleotide primers are employed to amplify the sequence isolated by the above methods. The 5' primer is 20 nucleotides long and the 3' primer is a complimentary sequence for the 3' end of the isolated mRNA. The primers are custom designed according to the isolated mRNA. The reverse transcriptase reaction and PCR amplification are performed sequentially without interruption in a Perkin Elmer 9600 PCR machine (Emeryville, Calif.). Four hundred ng total RNA in 20 µl diethylpyrocarbonate-treated water are placed in a 65° C. water bath for 5 min. and then quickly chilled on ice immediately prior to the addition of PCR reagents. The 50-µl total PCR volume consisted of 2.5 units Taq polymerase (Perkin-Elmer). 2 units avian myeloblastosis virus reverse transcriptase (Boehringer Mannheim, Indianapolis, Ind.); 200 µM each of dCTP, dATP, dGTP and dTTP (Perkin Elmer); 18 pM each primer, 10 mM Tris-HCl; 50 mM KCl; and 2 mM $MgCl_2$ (Perkin Elmer). PCR conditions are as follows: cycle 1 is 42° C. for 15 min then 97° C. for 15 s (1 cycle); cycle 2 is 95° C. for 1 min. 60° C. for 1 min, and 72° C. for 30 s (15 cycles); cycle 3 is 95° C. for 1 min. 60° C. for 1 min., and 72° C. for 1 min. (10 cycles); cycle 4 is 95° C. for 1 min., 60° C. for 1 min., and 72° C. for 2 min. (8 cycles); cycle 5 is 72° C. for 15 min. (1 cycle); and the final cycle is a 4° C. hold until sample is taken out of the machine. The 50-µl PCR products are concentrated down to 10 µl with vacuum centrifugation, and a sample is then run on a thin 1.2% Tris-borate-EDTA agarose gel containing ethidium bromide. A band of expected size would indicate that this gene is present in the tissue assayed. The amount of RNA in the pellet may be quantified in numerous ways, for example, it may be weighed.

Verification of the nucleotide sequence of the PCR products is done by microsequencing. The PCR product is purified with a Qiagen PCR Product Purification Kit (Qiagen, Chatsworth, Calif.) as described by the manufacturer. One µg of the PCR product undergoes PCR sequencing by using the Taq DyeDeoxy Terminator Cycle sequencing kit in a Perkin-Elmer 9600 PCR machine as described by Applied Biosystems (Foster, Calif.). The sequenced product is purified using Centri-Sep columns (Princeton Separations, Adelphia, N.J.) as described by the company. This product is then analyzed with an ABI model 373A DNA sequencing system (Applied Biosystems) integrated with a Macintosh IIci computer.

EXAMPLE 2

Bacterial Expression and Purification of the Colon Specific Gene Protein and Use for Preparing a Monoclonal Antibody The DNA sequence encoding a polypeptide of the present invention, ATCC # 97129, is initially amplified using PCR oligonucleotide primers corresponding to the 5' sequences of the processed protein (minus the signal peptide sequence) and the vector sequences 3' to the gene. Additional nucleotides corresponding to the DNA sequence are added to the 5' and 3' sequences respectively. The 5' oligonucleotide primer GCAGGATCCTGGCTTCCAGAAGCATG (BAMHI) (SEQ ID NO:3) may contain, for example, a restriction enzyme site followed by nucleotides of coding sequence starting from the presumed terminal amino acid of the processed protein. The 3' sequence TACGGGTACCT-TGCTCTATGGTCGGTAC (ASP718) (SEQ. ID NO:4) may, for example, contain complementary sequences to a restriction enzyme site and also be followed by nucleotides of the nucleic acid sequence encoding the protein of interest. The restriction enzyme sites correspond to the restriction enzyme sites on a bacterial expression vector, for example, pQE-32 (Qiagen, Inc. Chatsworth, Calif.). PQE-32 encodes antibiotic resistance (Amp'), a bacterial origin of replication (ori), an IPTG-regulatable promoter operator (P/O), a ribosome binding site (RBS), a 6-His tag and restriction enzyme sites. pQE-9 is then digested with the restriction enzymes corresponding to restriction enzyme sites contained in he primer sequences. The amplified sequences are ligated into pQE-9 and inserted in frame with the sequence encoding for the histidine tag and the RBS. The ligation mixture is then used to transform an E. coli strain, for example, M15/rep 4 (Qiagen) by the procedure described in Sambrook, J. et al., Molecular Cloning: A Laboratory Manual, Cold Spring Laboratory Press, (1989). M15/rep4 contains multiple copies of the plasmid pREP4, which expresses the laci repressor and also confers kanamycin resistance (Kan'). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized protein is purified from this solution by chromatography on a Nickel-Chelate column under conditions that allow for tight binding by proteins containing the 6-His tag (Hochuli, E. et al., J. Chromatography 411:177–184 (1984)). The protein is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

The protein purified in this manner may be used as an epitope to raise monoclonal antibodies specific to such protein. The monoclonal antibodies generated against the polypeptide the isolated protein can be obtained by direct injection of the polypeptides into an animal or by administering the polypeptides to an animal. The antibodies so obtained will then bind to the protein itself. Such antibodies can then be used to isolate the protein from tissue expressing that polypeptide by the use of an, for example, ELISA assay.

EXAMPLE 3

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 4

Cloning and Expression of Colon Specific Gene Polypeptide Using the Baculovirus Expression System The DNA sequence encoding the full length protein, ATCC # 97129, was amplified using PCR oligonucleotide primers corresponding to the 5' and 3' sequences of the gene:

The 5' primer has the sequence 5' ATCGGGATCCGC-CATC<u>ATG</u> GCTTCCAGAAGCATGCG (SEQ ID NO:5) and contains a BamHI restriction enzyme site (in bold) followed by 6 nucleotides resembling an efficient signal for the initiation of translation in eukaryotic cells (Kozak, M., J.

Mol. Biol., 196:947–950 (1987) which was just behind the first 20 nucleotides of the colon specific gene (the initiation codon for translation "ATG" was underlined).

The 3' primer has the sequence 5' TACGGGTACCT-TGCTC TATGGTCGGTAC 3' (SEQ ID NO:6) and contains the cleavage site for the restriction endonuclease Asp718 and 5 nucleotides complementary to the 3' non-translated sequence of the colon specific gene. The amplified sequences were isolated from a 1% agarose gel using a commercially available kit ("Geneclean," BIO 101 Inc., La Jolla, Calif.). The fragment was then digested with the endonucleases BamHI and Asp718 and then purified again on a 1% agarose gel. This fragment was designated F2.

The vector pA2 (modification of pVL941 vector, discussed below) was used for the expression of the colon specific protein using the baculovirus expression system (for review see: Summers, M. D. and Smith, G. E. 1987, A manual of methods for baculovirus vectors and insect cell culture procedures, Texas Agricultural Experimental Station Bulletin NO:1555). This expression vector contains the strong polyhedrin promoter of the *Autographa californica* nuclear polyhedrosis virus (AcMNPV) followed by the recognition sites for the restriction endonucleases BamHI and Asp718. The polyadenylation site of the simian virus (SV)40 was used for efficient polyadenylation. For an easy selection of recombinant viruses the beta-galactosidase gene from *E.coli* was inserted in the same orientation as the polyhedrin promoter followed by the polyadenylation signal of the polyhedrin gene. The polyhedrin sequences were flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA was designated V2.

Fragment F2 and the dephosphorylated plasmid V2 were ligated with T4 DNA ligase. DH5α cells were then transformed and bacteria identified that contained the plasmid (pBac-colon specific polypepitde) with the colon specific gene using the enzymes BamHI and Asp718. The sequence of the cloned fragment was confirmed by DNA sequencing.

5 μg of the plasmid pBac-colon specific gene was cotransfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBac-colon specific gene were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 27 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells and blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-colon specific gene at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The colon specific protein was purified from infected cells 72 hours post infection by cell lysis in hypotonic phosphate buffer and further purified by ion exchange chromatography, size exclusion chromatography, and reverse phase chromatography.

Numerous modifications and variations of the present invention were possible in light of the above teachings and, therefore, within the scope of the appended claims, the invention may be practiced otherwise than as particularly described.

What is claimed is:

1. A purified protein comprising amino acids 2 to 158 of SEQ ID NO:2.

2. The purified protein of claim 1 which comprises amino acids 1 to 158 of SEQ ID NO:2.

3. The purified protein of claim 1 which comprises a heterologous polypeptide sequence.

4. A composition comprising the purified protein of claim 1 and a pharmaceutically acceptable carrier.

5. A purified protein comprising a polypeptide sequence of 10 contiguous amino acids of SEQ ID NO:2, wherein said polypeptide sequence binds an antibody specific to the polypeptide of SEQ ID NO:2.

6. The purified protein of claim 5 which comprises a polypeptide sequence of 30 contiguous amino acids of SEQ ID NO:2, wherein said polypeptide sequence binds an antibody specific to the polypeptide of SEQ ID NO:2.

7. The purified protein of claim 5 which comprises a polypeptide sequence of 50 contiguous amino acids of SEQ ID NO:2, wherein said polypeptide sequence binds an antibody specific to the polypeptide of SEQ ID NO:2.

8. The purified protein of claim 5 which comprises a heterologous polypeptide sequence.

9. A composition comprising the purified protein of claim 5 and a pharmaceutically acceptable carrier.

10. A purified protein comprising a polypeptide sequence selected from the group consisting of:

(a) the amino acid sequence of full-length polypeptide encoded by the human cDNA contained in ATCC Deposit No. 97129; and (b) the amino acid sequence of the mature polypeptide encoded by the human cDNA contained in ATCC Deposit No. 97129.

11. The purified protein of claim 10 wherein said polypeptide sequence is (a).

12. The purified protein of claim 10 wherein said polypeptide sequence is (b).

13. The purified protein of claim 10 which comprises a heterologous polypeptide sequence.

14. A composition comprising the purified protein of claim 10 and a pharmaceutically acceptable carrier.

15. A purified protein comprising a polypeptide sequence of 10 contiguous amino acids of the full-length polypeptide, wherein said polypeptide sequence binds an antibody specific to the polypeptide of SEQ ID NO:2 encoded by the human cDNA contained in ATCC Deposit No. 97129.

16. The purified protein of claim 15 which comprises a polypeptide sequence of 30 contiguous amino acids of the full-length polypeptide encoded by the human cDNA contained in ATCC Deposit No. 97129.

17. The purified protein of claim 15 which comprises a polypeptide sequence of 50 contiguous amino acids of the full-length polypeptide encoded by the human cDNA contained in ATCC Deposit No. 97129.

18. The purified protein of claim 15 which comprises a heterologous polypeptide sequence.

19. A composition comprising the purified protein of claim 15 and a pharmaceutically acceptable carrier.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1114 BASE PAIRS

```
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:1:

GCACGAGGCC AAACAGATTT GCAGATCAAG GAGAACCCAG GAGTTTCAAA GAAGCGCTAG      60

TAAGGTCTCT GAGATCCTTG CACTAGCTAC ATCCTCAGGG TAGGAGGAAG ATGGCTTCCA     120

GAAGCATGCG GCTGCTCCTA TTGCTGAGCT GCCTGGCCAA AACAGGAGTC CTGGGTGATA     180

TCATCATGAG ACCCAGCTGT GCTCCTGGAT GGTTTTACCA CAAGTCCAAT TGCTATGGTT     240

ACTTCAGGAA GCTGAGGAAC TGGTCTGATG CCGAGCTCGA GTGTCAGTCT TACGGAAACG     300

GAGCCCACCT GGCATCTATC CTGAGTTTAA AGGAAGCCAG CACCATAGCA GAGTACATAA     360

GTGGCTATCA GAGAAGCCAG CCGATATGGA TTGGCCTGCA CGACCCACAG AAGAGGCAGC     420

AGTGGCAGTG GATTGATGGG GCCATGTATC TGTACAGATC CTGGTCTGGC AAGTCCATGG     480

GTGGGAACAA GCACTGTGCT GAGATGAGCT CCAATAACAA CTTTTTAACT TGGAGCAGCA     540

ACGAATGCAA CAAGCGCCAA CACTTCCTGT GCAAGTACCG ACCATAGAGC AAGAATCAAG     600

ATTCTGCTAA CTCCTGCACA GCCCCGTCCT CTTCCTTTCT GCTAGCCTGG CTAAATCTGC     660

TCATTATTTC AGAGGGGAAA CCTAGCAAAC TAAGAGTGAT AAGGGCCCTA CTACACTGGC     720

TTTTTTAGGC TTAGAGACAG AAACTTTAGC ATTGGCCCAG TAGTGGCTTC TAGCTCTAAA     780

TGTTTGCCCC GCCATCCCTT TCCACAGTAT CCTTCTTCCC TCCTCCCCTG TCTCTGGCTG     840

TCTCGAGCAG TCTAGAAGAG TGCATCTCCA GCCTATGAAA CAGCTGGGTC TTTGGCCATA     900

AGAAGTAAAG ATTTGAAGAC AGAAGGAAGA AACTCAGGAG TAAGCTTCTA GACCCCTTCA     960

GCTTCTACAC CCTTCTGCCC TCTCTCCATT GCCTGCACCC CACCCCAGCC ACTCAACTCC    1020

TGCTTGTTTT TCCTTTGGCC ATAGGAAGGT TTACCAGTAG AATCCTTGCT AGGTTGATGT    1080

GGGCCATACA TTCCTTTAAT AAACCATTGT GTAC                                1114

(2) INFORMATION FOR SEQ ID NO:2:

(i) SEQUENCE CHARACTERISTICS:
        (A) LENGTH: 158 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

Met Ala Ser Arg Ser Met Arg Leu Leu Leu Leu Ser Cys Leu
                5                  10                  15

Ala Lys Thr Gly Val Leu Gly Asp Ile Ile Met Arg Pro Ser Cys
         20                  25                  30

Ala Pro Gly Trp Phe Tyr His Lys Ser Asn Cys Tyr Gly Tyr Phe
         35                  40                  45

Arg Lys Leu Arg Asn Trp Ser Asp Ala Glu Leu Glu Cys Gln Ser
         50                  55                  60

Tyr Gly Asn Gly Ala His Leu Ala Ser Ile Leu Ser Leu Lys Glu
         65                  70                  75

Ala Ser Thr Ile Ala Glu Tyr Ile Ser Gly Tyr Gln Arg Ser Gln
         80                  85                  90

Pro Ile Trp Ile Gly Leu His Asp Pro Gln Lys Arg Gln Gln Trp
         95                 100                 105
```

```
Gln Trp Ile Asp Gly Ala Met Tyr Leu Tyr Arg Ser Trp Ser Gly
            110                 115                 120

Lys Ser Met Gly Gly Asn Lys His Cys Ala Glu Met Ser Ser Asn
            125                 130                 135

Asn Asn Phe Leu Thr Trp Ser Ser Asn Glu Cys Asn Lys Arg Gln
            140                 145                 150

His Phe Leu Cys Lys Tyr Arg Pro
            155
```

(2) INFORMATION FOR SEQ ID NO:3:

(i) SEQUENCE CHARACTERISTICS:
        (A) LENGTH: 26 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

GCAGGATCCT GGCTTCCAGA AGCATG                                          26

(2) INFORMATION FOR SEQ ID NO:4:

(i) SEQUENCE CHARACTERISTICS:
        (A) LENGTH: 28 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:4:

TACGGGTACC TTGCTCTATG GTCGGTAC                                      28

(2) INFORMATION FOR SEQ ID NO:5:

(i) SEQUENCE CHARACTERISTICS:
        (A) LENGTH: 36 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:5:

ATCGGGATCC GCCATCATGG CTTCCAGAAG CATGCG                          36

(2) INFORMATION FOR SEQ ID NO:6:

(i) SEQUENCE CHARACTERISTICS:
        (A) LENGTH: 28 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:6:

TACGGGTACC TTGCTCTATG GTCGGTAC                                      28